United States Patent [19]

Burns et al.

[11] Patent Number: 5,576,215

[45] Date of Patent: Nov. 19, 1996

[54] ADAPTIVE SCHEDULING SYSTEM AND METHOD FOR OPERATING A BIOLOGICAL SAMPLE ANALYZER WITH VARIABLE INTERVAL PERIODS

[75] Inventors: Kathleen L. Burns, Hawthorne Woods; Ilya Ratner, Highwood; Jeanine T. Douglas, Gurnee; Erica J. Kline, Grayslake; Cass J. Grandone, Lake Forest, all of Ill.

[73] Assignee: Abbott Laboratories, Abbott Park, Ill.

[21] Appl. No.: 709,723

[22] Filed: Jun. 3, 1991

[51] Int. Cl.⁶ .................................................. G01N 35/10
[52] U.S. Cl. ............................ 436/50; 422/63; 422/64; 422/67; 422/116; 436/47; 436/49; 436/807; 364/497; 364/500
[58] Field of Search .................................. 422/67, 63–66, 422/166; 436/43, 47, 50, 807, 55, 49; 364/497, 500

[56] References Cited

U.S. PATENT DOCUMENTS

| | | |
|---|---|---|
| 3,497,320 | 2/1970 | Blackburn et al. |
| 3,597,161 | 8/1971 | Greiner . |
| 3,660,638 | 5/1972 | Oberli . |
| 3,728,080 | 4/1973 | Moran . |
| 3,770,382 | 11/1973 | Carter et al. . |
| 3,799,744 | 3/1974 | Jones . |
| 3,874,850 | 4/1975 | Sorensen et al. . |
| 4,054,416 | 10/1977 | Duff . |
| 4,058,367 | 11/1977 | Gilford . |
| 4,113,436 | 9/1978 | Werder et al. ............... 422/65 |
| 4,265,855 | 5/1981 | Mandle et al. ............... 422/65 |
| 4,303,611 | 12/1981 | Jessop ........................ 422/65 |
| 4,326,851 | 3/1982 | Bello et al. . |
| 4,370,983 | 2/1983 | Lichtenstein ............... 128/630 |
| 4,383,041 | 5/1983 | Kutsusawa et al. ........ 435/291 |
| 4,416,995 | 11/1983 | Amaral ....................... 435/291 |
| 4,595,562 | 6/1986 | Liston et al. ................. 422/65 |
| 4,603,114 | 7/1986 | Hood et al. .................. 436/89 |
| 4,655,225 | 4/1987 | Dähne et al. ............... 128/633 |
| 4,678,752 | 7/1987 | Thorne et al. .............. 435/291 |
| 4,766,550 | 8/1988 | Byers et al. ................ 364/497 |
| 4,795,613 | 1/1989 | Azuma et al. ............... 422/64 |
| 4,835,110 | 5/1989 | Seymour et al. ........... 436/517 |
| 4,910,691 | 3/1990 | Skeirik ...................... 364/513 |
| 4,971,900 | 11/1990 | Ahnell et al. ................ 435/29 |
| 4,995,402 | 2/1991 | Smith et al. ................ 128/771 |
| 5,025,389 | 6/1991 | Imai .......................... 364/497 |
| 5,104,808 | 4/1992 | Laska et al. ................ 436/48 |

OTHER PUBLICATIONS

"ADx® System Operator's Guide", by Abbott Laboratories, Diagnostics Division, 1987, 1988, 1989, 1990, pp. R–105 19 to R–105 26; R–105 2–10; R–105 4–4; and R–105 4–10 to R–105 4–45.

*Primary Examiner*—Jill A. Johnston
*Assistant Examiner*—Long V. Le
*Attorney, Agent, or Firm*—Richard D. Schmidt

[57] ABSTRACT

An improved biological sample analyzer, and a method and system for operation thereof, wherein instrument systems used to perform assays of the biological samples loaded into the analyzer are operated in accordance with a schedule developed by a scheduler routine. The scheduler routine determines interval periods between operations performed by the analyzer instrument systems on each biological sample as a function of an entered load list unless a fixed interval period between the operations is required and schedules instrument system operations and the determined interval periods. The biological system analyzer performs assays of the biological samples by operating the analyzer instrument systems in accordance with the developed schedule.

30 Claims, 6 Drawing Sheets

Microfiche Appendix Included
(2 Microfiche, 139 Pages)

ADAPTIVE SCHEDULING SYSTEM AND
METHOD FOR OPERATING A BIOLOGICAL
SAMPLE ANALYZER WITH VARIABLE
INTERVAL PERIODS

MICROFICHE APPENDIX

Included are two microfiche of 139 total frames.

REFERENCE TO RELATED APPLICATIONS

The disclosures of the following copending applications assigned to the assignee of the present application and filed concurrently herewith are specifically incorporated by reference:

"Adaptive Scheduling System and Method For a Biological Analyzer With Reproducible Operation Time Periods", by Cass J. Grandone, Mark Pierce, Ilya Ratner, and Jeanine T. Douglas application Ser. No. 07/709,721, filed Jun. 3, 1991, now U.S. Pat. No. 5,282,149;

"Adaptive Scheduling System and Method For Operating a Biological Sample Analyzer With Variable Rinsing", by Cass J. Grandone application Ser. No. 07/710,195, filed Jun. 3, 1991, now U.S. Pat. No. 5,289,385;

"Retrofit Kit For Changing Single Immunoassay Instrument to Flexible Multiple Immunoassay Instrument", by Chadwick M. Dunn, Cass J. Grandone, Stephen L. Herchenback, Robert J. Nelson, Robert Perry, James T. Tyranski and Gary Lee Zuck application Ser. No. 07/709,730, filed Jun. 5, 1991;

"Carousel For Assay Specimen Carrier", by Cass J. Grandone, Steven L. Herchenback, Robert Perry, James T. Tyranski and Gary Lee Zuck application Ser. No. 07/709,724, filed Jun. 3, 1991;

"Heat and Air Flow Control For Assay Carrier", by Chadwick M. Dunn, Cass J. Grandone, James T. Tyranski and Kris T. Luddington application Ser. No. 07/709,728, filed Jun. 3, 1991, now U.S. Pat. No. 5,246,665;

"Reagent Bottle and Cap", by James T. Tyranski application Ser. No. 07/709,725, filed Jun. 3, 1991, now U.S. Pat. No. 5,145,646; and "Reagent Pack For Immunoassays", by Steven Herchenback, Robert Nelson, James T. Tyranski and Gary Lee Zuck application Ser. No. 07/709,726, filed Jun. 3, 1991.

BACKGROUND OF THE INVENTION

The present invention relates generally to biological sample analyzers used to perform assays of patient specimen samples. More particularly, the present invention relates to a method and system for the scheduling the operating steps for performing assays of biological samples in an automatic analyzer.

Biological sample analyzers, of the type considered herein, are automated instruments that may be used in hospitals, clinics, laboratories, doctors' offices, testing clinics, or other locations, to run routine tests (assays) on samples of patient specimens such as blood, spinal fluid, urine, serum, plasma, and so on. An automated analyzer of the type discussed herein includes an analyzer unit that runs tests on a number of patient specimen samples that are loaded into the unit. An operator-user prepares the samples by placing portions of the patients' specimen samples into a number of like-sized sample containers. These samples may be diluted or otherwise treated, depending upon the type of analyzer used, the type of assay being performed, and other factors. The containers are then placed in the analyzer unit. The containers may first be placed in a rack or carousel that is then placed in the analyzing unit. The rack may accommodate a number of sample containers, e.g. 24. In addition, one or more appropriate chemical reagents, needed to perform the assays, are also placed in the analyzer unit. In order to mix reagents with the samples, the analyzer unit may also include a fluid moving system, such as a robotic probe mounted on a boom, which is adapted to draw up portions of the reagents and/or samples and expel them into appropriate locations, e.g. additional cells such as reaction cells provided in the sample containers, where a reaction can take place. The analyzer unit also may include a means for detecting a reaction in the reaction cells. This may include an optical detector to observe fluorescence reactions and make optical measurements to obtain a result for each sample. The analyzer unit may also typically include other mechanical systems to move the sample containers and the probe. The analyzer unit may also provide for cleaning the probe between certain tasks in order to avoid contamination between samples. For this purpose, the analyzer unit may also include a washing station and a waste dispensing container to hold the used rinse solution.

After the operator-user loads the specimen samples, enters appropriate instructions, and starts the unit, the analyzer runs unattended. When placed in operation, the analyzer unit, using the appropriate chemical reagent, runs the same test on each of the samples in the sample containers and will perform identical operations on each of the samples loaded in the rack. When it is finished, the analyzer prints out or otherwise reports on the results of its testing.

Biological analyzers utilize different chemistries for performing assays of specimen samples. One type of assays used in biological analyzers includes immunoassays and solid phase procedures. Analyzers for performing immunoassays in general and enzyme immunoassays in particular are known in the art.

A biological analyzer that utilizes immunoassay chemistry to perform assays of specimen samples loaded therein is the IMx® analyzer introduced in 1988 by Abbott Laboratories, of North Chicago, Ill. (A description of the IMx analyzer is included in "The Abbott IMx Automated Benchtop Immunochemistry Analyzer System", by Fiore, M. et al., *Clinical Chemistry*, Vol. 34, No. 9, 1988, which is specifically incorporated herein by reference in its entirety). The IMx analyzer is a biological sample analyzer that has been developed for use in conjunction with solid phase immunoassay procedures to perform a variety of assays (such as sandwich and competitive assays). The IMx analyzer uses a technology referred to as microparticle capture enzyme immunoassay (MEIA) and fluorescence polarization immunoassay (FPIA). The IMx analyzer includes a microprocessor used to control a robotic arm with 2 degrees of freedom and a rotating carousel to process the samples for assay. One assay can be done on each of 24 specimen samples in 30–40 minutes or more unattended after loading (i.e. with "walk away" automation). Assay results are output to a printer or a computer interface.

A biological sample analyzer, such as the IMx analyzer described above, can execute the steps required for performing assays of up to 24 specimen samples, including the steps of counting the samples, identifying which assay to run, warming the reagents and reaction cells to appropriate temperatures, pipetting the reagents and samples, diluting samples if required, timing critical assay steps such as incubations, washing unbound conjugate, quantifying the fluorescence signal and performing data reduction to yield a useful result.

The container used for holding each of the specimen samples for a biological sample analyzer, such as the IMx analyzer, may be a disposable assay cartridge having a plurality of wells, with at least one reaction well and one separation well. The separation well may contain a fibrous matrix positioned across its entrance and an absorbent material positioned below the fibrous matrix. Microparticles react with a sample and one or more reagents to form a complex. This complex is immobilized on the matrix of the separation well of the matrix. The excess sample and reagent are washed through the matrix and captured in the absorbent material below.

The results of the reactions may be read using known optical detection techniques. For example, using conventional solid phase procedures, an analyte can be labeled or tagged with an enzyme which, when in the presence of its substrate, fluoresces and emits light at a known wave length. The rate at which the fluorescent product is produced is indicative of the concentration of the analyte in the biological sample. A conventional fluorometer is suitable for illuminating the fibrous matrix with a beam of light having the appropriate excitation wave length. The fluorometer also detects the intensity of the light at the emission wave length. Assays using this type of solid phase technology has been found to provide a high degree of sensitivity.

A biological sample analyzer, such as the IMx analyzer, provides for performing assays of patients' specimen samples and reading the results of such assays in a mass production type manner. This allows such assays to be made available quickly and conveniently.

Even though such analyzers can provide significant advantages by performing assays quickly and conveniently, further advantages for the user could be obtained if the overall through put of the analyzer could be increased. One way to provide even more advantages and convenience for users of biological analyzers would be to provide the capability to perform more than one assay on the specimen samples in an unattended run. Although a biological analyzer like the IMx analyzer can perform different types of assays and can perform assays on a number of specimen samples unattended, the analyzer can run only one type of assay at a time. If a different type of assay is to be performed, the analyzer would have to be reloaded with different reagents. Also, because different types of assays may require different amounts of the sample specimen, different amounts of reagents, different processing steps, different incubation times, etc., the analyzer would also be reset at the beginning of the run to perform the new assay. In the case of the IMx analyzer, a different memory module may have to be inserted containing the instructions for the analyzer unit for performing the different assay. Thus, even if only a few of several different types of assays need to be run, the operator-user has to load and run the analyzer for the first type of assay for only a few samples and then reload the analyzer to run the second type of assay on another batch of samples using perhaps different reagents. It is recognized that for many users of the IMx analyzer, or other biological sample analyzers, it would be convenient and advantageous to be able to perform more than one type of assay during an unattended run.

Although it may be desirable to provide a biological analyzer with the capability to perform more than one assay in an unattended run, there are several obstacles that make providing this feature complicated. For example, different assays require different functions or operations to be performed upon the sample specimens in the carousel rack by the mechanical or optical systems of the analyzer. In the prior IMx analyzer, or in other analyzers in which only one type of assay is being performed during an unattended run, it could be predicted when each of the operations upon each of the samples will be performed and sufficient time allowance can be provided to ensure that incubation period limits are not exceeded or that the samples or reagents do not evaporate. This is difficult to do in an analyzer in which the user is permitted to select the type and number of assays to be performed in an unattended run. For example, if there are up to 24 specimen samples in the carousel rack and the operator-user is permitted to select any one of three different assays to be performed on the samples, there are almost 2500 different permutations of possible combinations of assays and samples that the user can select. (The number is 2925 if all possible combinations, even those that an operator-user would never run are considered). If the operator-user is permitted to select any one of four different assays to be performed on the up to 24 samples, there are approximately 10,000 different permutations of possible combinations. This presents an operating problem because certain tasks in the automatic analyzer must be performed on the samples at certain times or within certain specific time limits. Thus, there is a requirement to efficiently schedule the activities being performed by the automatic analyzer. Considering that 100 or more different mechanical operations can be performed on each sample, and that due to chemical reaction constraints certain operations must be performed within certain rigidly specified time durations from other operations in order to obtain valid results, it can readily be appreciated that scheduling and operating an analyzer to perform more than one assay unattended is considerably more complicated than scheduling and operating an analyzer in which only one assay is performed in an unattended run.

One automatic assay device is known having the capability to perform more than one assay on specimen samples loaded therein in an unattended (e.g. "walk-away") run. That device is the ADx® biological analyzer available from Abbott Laboratories. Although the ADx analyzer can perform more than one type of assay on samples loaded in its carousel rack, the ADx analyzer is used primarily for assays that are different than those performed by the IMx analyzer. The assays performed by the ADx analyzer are, in general, simpler and typically include fewer steps. Also with respect to the assays performed by the ADx analyzer, there are, in general, fewer constraints on incubation periods between steps. Accordingly, when the ADx biological sample analyzer is used to perform more than one assay in a run, the scheduling of the various operations to be performed by the analyzer systems on the specimen samples can be accomplished by using the minimum incubation time interval between operations. However, when the minimum incubation period is used, the throughput of the analyzer can decrease (i.e., the overall time to run the assays increases) due to conflicts among the schedules of the assays. By contrast, with the type of assays performed by the IMx, such as MEIA and FPIA, there are usually a greater number of steps for each assay and there are more constraints that certain steps must be performed within certain incubation time limits to produce valid data. Moreover, with the types of assays performed on the IMx analyzer, there is also greater variability in the assay steps and incubation limits between different steps among different assays. Accordingly, it is difficult to schedule an analyzer such as the IMx analyzer to perform more than one assay in an unattended run.

Accordingly, it is an object of the present invention to provide a method and system for operating a biological sample analyzer to automatically perform more than one type of assay on patient specimen samples loaded therein in accordance with defined incubation time constraints and with reasonably good through put.

SUMMARY OF THE INVENTION

The present invention provides a biological sample analyzer, and a method and system for operation thereof, wherein instrument systems used to perform assays of the biological samples loaded into the analyzer are operated in accordance with a schedule developed by a scheduler routine. The scheduler routine determines interval periods between operations performed by the analyzer instrument systems on each biological sample as a function of an entered load list unless a fixed interval period between the operations is required and schedules instrument system operations and the determined interval periods. The biological system analyzer performs assays of the biological samples by operating the analyzer instrument systems in accordance with the developed schedule.

According to an embodiment, an operator-user can use the analyzer efficiently and conveniently to perform more-than-one type of assay on the biological samples loaded into the analyzer in an unattended run without emptying or reloading the instrument and resetting the automatic analyzing machine.

For purposes of this specification and claims, a "run" is considered to refer to the operation of the analyzer in performing the assays after the operator-user has loaded into the analyzer the specimen samples, reagents, rinse, or other accessory material and also entered any necessary information pertaining to the assays to be performed on the samples. The "run" concludes when the assays have been performed on all the samples and may include data analysis performed in generating an assay test result or printing or otherwise outputting the results of the assays. In automatic analyzers of the type considered herein, the run may proceed unattended.

DETAILED DESCRIPTION OF THE PRESENTLY PREFERRED EMBODIMENTS

Figure 1:
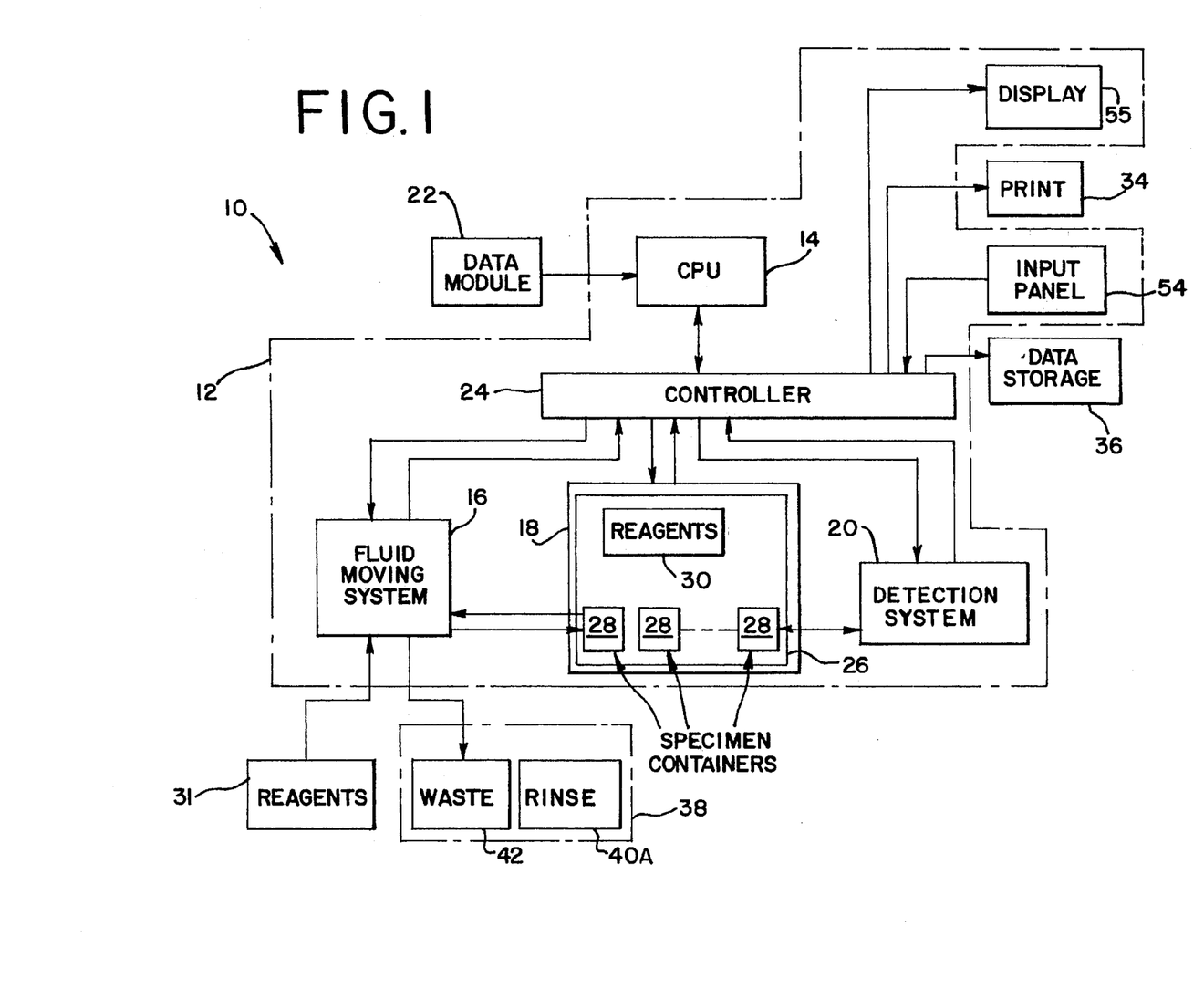
FIG. 1 is schematic of a biological sample analyzer incorporating aspects of a first presently preferred embodiment of the present invention.

Referring to FIG. 1, there is depicted a schematic block diagram of a biological sample analyzer 10 of a first embodiment of the present invention. The biological system analyzer 10 includes an analyzer unit 12, in which is included a CPU 14. The CPU 14 operates analyzer unit instrument systems in accordance with means well known to those skilled in the art. The analyzer unit instrument systems include a fluid moving system 16, a carousel moving system 18, and a detection system 20. Additional systems may also be included. One or more modules 22 include programming, stored for example in a PROM, used for the operation of the analyzer unit 12 and the analyzer unit systems. The programming on these modules 22 may include separate programs specifically adapted for performing specific different types of assays. These modules 22 may be removable to provide for additional different assays to be performed as well as to readily provide for updates and improvements to the system operation to be implemented. The analyzer unit instrument systems 16, 18 and 20 operate through an appropriate controller-interface 24. In this embodiment, the CPU 14 used is an Intel Model 80286 microprocessor.

The carousel moving system 18 is adapted to move a carousel or rack 26 upon which is positioned a plurality of patient specimen sample containers 28. The carousel 26 is preferably removable in order to facilitate loading and unloading of the patient specimen sample containers 28 into the analyzer unit 12. The carousel 26 may also hold a first set of one or more reagents 30 for performing a particular assay. A second set of one or more reagents 31 may also be included in the analyzer unit 12 in a location off of the carousel 26. These reagents may be in reagent packs and may include reagents for performing MEIA and/or FPIA types of assay tests, as described above.

The fluid moving system 16 includes one or more robotic pipette-booms adapted to move fluid from one location to another in the analyzer unit 12, e.g. from one container to another, under the control of the CPU 14.

The CPU 14 operates the carousel moving system 18 to move the carousel 26 and the fluid moving system 16 to move the pipette-boom to mix the appropriate reagents with the specimen samples in the containers 28. The CPU 14 also operates the carousel moving system 18 to move the carousel 26 and thereby the containers 28 into position to observe reactions at the detection system 20. The CPU 14 controls the detection system 20 which may include means for detecting florescence in a manner that is well known in the art. In a preferred embodiment, the detection system 20 includes a low pressure mercury lamp used in a fluorometer. The CPU 14 receives the information about the reactions from the detection system 20 and performs the appropriate data analysis, and outputs results to either a printer 34 or to a data storage 36. A cleaning station 38 may also be provided in the analyzer unit 12. The cleaning station 38 includes a rinsing solution 40 and a waster container 42 into which waste fluid can be dispelled.

Figure 2:
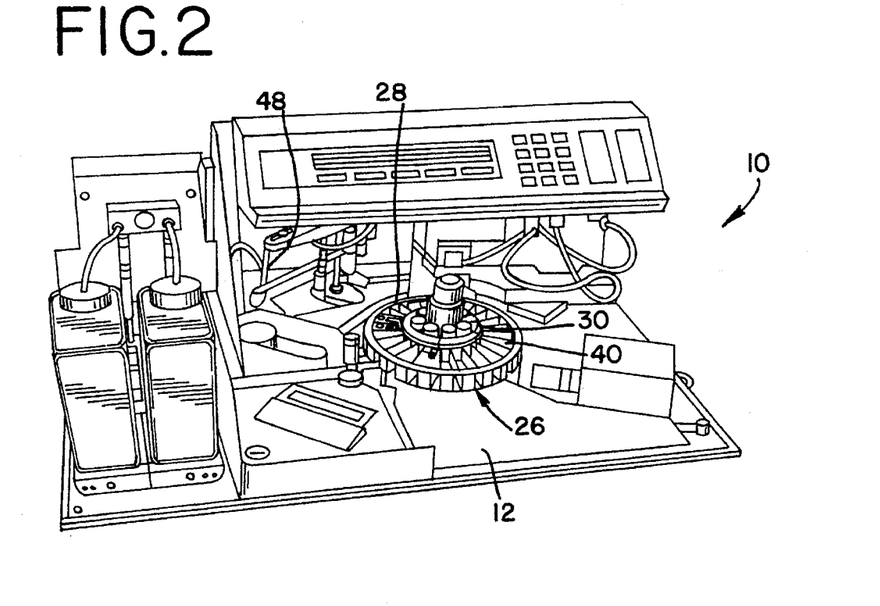
FIG. 2 is perspective view of a biological sample analyzer (with a cover portion removed to reveal components therein) of the embodiment of FIG. 1.

Referring to FIG. 2, there is depicted a perspective view of the biological sample analyzer 10 incorporating aspects of the first embodiment of the present invention. The analyzer unit 12 holds the circular carousel rack 26 into which are placed a plurality of assay container cartridges 28. These cartridges 28 are preferably disposable. The assay container cartridges 28 are placed in a plurality of openings 40 (also referred to as "wedges") arranged around a central core of the carousel rack 26 which is specially formed to hold the cartridges. All the cartridge containers 28 have individual alignment features that insure their accurate alignment within the rack 26.

The carousel rack 26 containing the cartridge containers 28 can be circularly indexed to accurately position each assay cartridge container relative to the detection system 20 containing a optical reading apparatus. Because the reading positioning is highly accurate, the assay is properly positioned for reading at a reading station.

The fluid moving system 16 includes a pipette/probe assembly that include syringes 48 (e.g. a 250 microliter sample syringe and a 2500 microliter diluent syringe may be provided) driven by stepper motors. The pipette/probe assembly can be positioned over the reagents 30 or 31, the individual wells of the containers 28, or the wash station 38. Stepper motors move the pipette system up and down as well as radially. The fluid moving system 16 transfers fluid from reagent bottles to the container 28 and from well to well within the container. The pipette itself is a drawn stainless steel tube, teflon coated to minimize carryover. Fluid levels may be sensed by measuring electrical conductivity between the pipette pro tip and an externally electrode.

Carryover between samples and reagents is minimized by washing the pipette/probe over a wash station.

Because enzyme immunoassays require precise temperature control to achieve repeatable performance, heating elements (not shown) are provided in the analyzer unit 12.

The biological analyzer 10 illustrated in FIG. 2 is similar to the prior analyzer (the IMx analyzer) sold by Abbott Laboratories, Inc. Compared to the prior analyzer, this embodiment of the analyzer includes additional reagents 30 that are stored in the carousel 26 in the analyzer and are used to perform the greater-than-one assays during a run. The description of the details of construction of the analyzer are disclosed to help define the environment of the present invention and such details do not form part of the invention. This embodiment of the analyzer also includes additional programming to perform the greater-than-one assays during a run.

Figure 3:
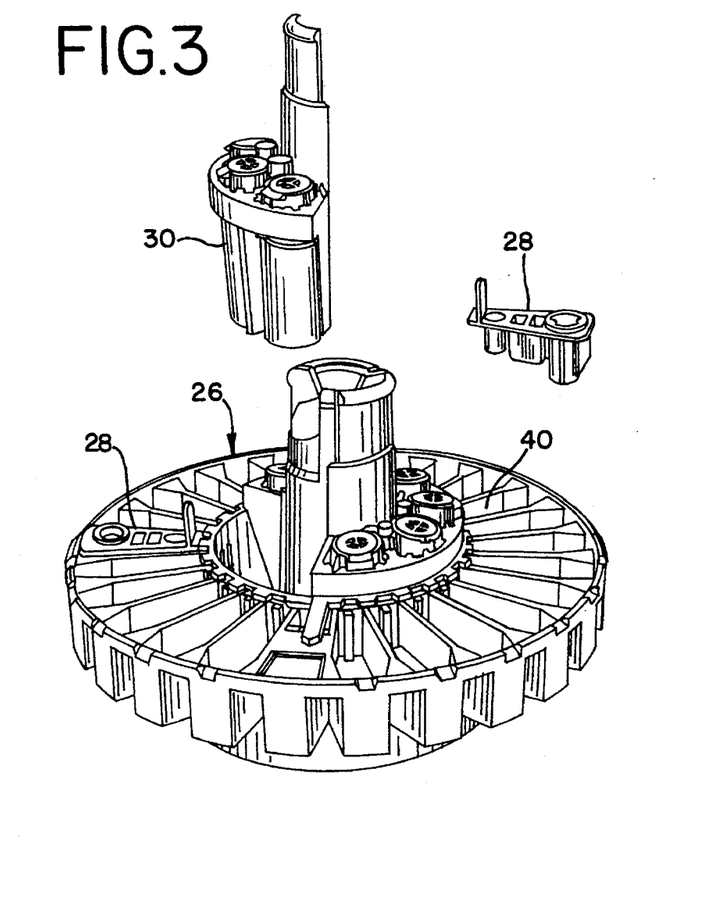
FIG. 3 is a perspective view of the carousel rack of the embodiment shown in FIG. 2.

As shown in FIG. 3, a first set of reagents 30 is included on the carousel 26. In a preferred embodiment, these reagents 30 are included on a portion of the carousel 26 and located centrally of the sample wedges 40.

An operator-user prepares for an assay run sequence by loading containers containing patient specimen samples (sometimes referred to as "disposables") into the carousel 26. In this embodiment, approximately 150 microliters of sample, controls, or calibrators is added to a sample well of each of the reaction cells of the container. The carousel rack is then placed in the analyzer unit 12 and the appropriate reagent pack or packs are loaded into the unit or the carousel.

In this embodiment of the analyzer 10, the operator-user also includes a calibration sample for each assay type being run. Thus, if three different types of assays are being run, three separate calibration samples are also run. The calibration samples have a known amount of the substance being tested for, and accordingly, are used as a basis for determining the amounts of the tested for substance in the unknown specimen samples by comparison of the reactions. This use of calibration samples is similar to what has been performed in the prior IMx analyzer. Typically, the calibration samples occupy specific positions (i.e. wedges) in the carousel rack 26.

The operator-user enters a load list. This may be done by means of the input panel 54 (of FIG. 1). The entry of the load list may be prompted by a menu on the display 55. The load list identifies the wedges of the carousel in which patient specimen samples are located and which assay is to be run on each of the specimen samples. Not all of the wedges of the carousel have to be used. The operator-user has the option of selecting several different assays to be performed automatically in a single run and also has the option of selecting the number of specimen samples to be used for each different assay. In a preferred embodiment up to four different assays may be available, however, the present invention could be extended to even a greater number. In a preferred embodiment, the samples upon which the same assay is to be performed are grouped together, i.e. in adjacent wedges of the carousel. This facilitates input of the load list by allowing the operator-user to indicate at which wedge position the specimen samples for a specific assay begin.

For purposes of efficiency, certain types of assays will be typically grouped together. For example, the assays for Prolactin, LH and FSH will be typically grouped together and the tests for CEA, AFP, and CA 19-9 will be grouped together. Other grouping of assays can be provided. These grouping are based, in part, upon the likelihood that an operator-user would want to run these assays at the same time. These combinations could be changed to include other assays or delete assays if different combinations would be preferred. If a different combination of assays were included, the appropriate reagents for those assays would be loaded in the analyzer unit.

Although in a preferred embodiment, the user-operator enters a load list by inputting information into the input panel 54, the load list for a run may be entered by other means. For example, the load list could be entered via a computer or communications interface. Alternatively, the load list may be determined automatically by scanning information attached or otherwise associated with each specimen sample container.

After closing a door or otherwise performing any other steps for preparing the analyzer unit, the operator-user actuates a run button on the input panel 54 of the analyzer unit. From this point, the analyzer can operate automatically and unattended until all the assays are finished.

Under the control of a program run on the CPU 14, the analyzer unit 12 begins a preparation process in which the following actions typically are taken: all stepper motors (fluids, syringe pumps, carousel motor, pipette system motors) are positioned in the "home" position, the carousel rack is scanned to identify the type of carousel installed and its "lock" status. The reagent pack types are read by a bar code scanner located on the pipette system to identify or confirm the assays to be run. The carousel heating systems warm the reagents and reaction cells to the appropriate temperatures by directing heated air throughout the carousel as described above. The program also calls a scheduling program that schedules the operations to be performed by the instrument systems on the specimen samples.

Figure 4:
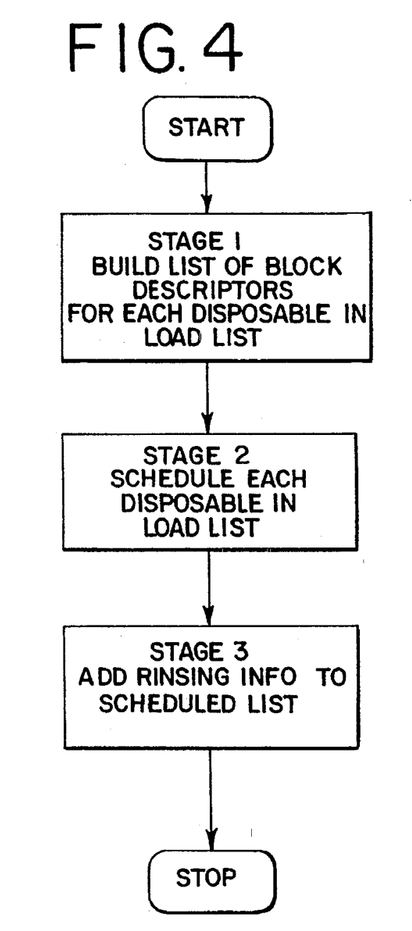
FIG. 4 is a block diagram flow chart depicting operating stages of a scheduler routine for operating the embodiment of the invention shown in FIG. 1.

FIG. 4 is a flow chart illustrating the program operation for the scheduler program 60 used to schedule the operations to be performed by the analyzer unit to perform the assays on the load list in accordance with one embodiment of the present invention. The scheduler program allows for scheduling the tasks performed by the analyzer in order to assure that certain tasks are performed within allowable time frames and with favorable through put. STAGE 1 includes procedures for creating a list of time blocks and a block descriptor for each time block, estimating the running time for each block, and sorting the load list. STAGE 2 includes procedures that establish the schedule of time blocks for each specimen sample so that the operations of a time block of a sample being scheduled do not conflict with any time blocks of any samples that have already been scheduled and that incubation limits between time blocks are not exceeded. STAGE 3 includes procedures for inserting rinsing information between or before time blocks.

Figure 5:
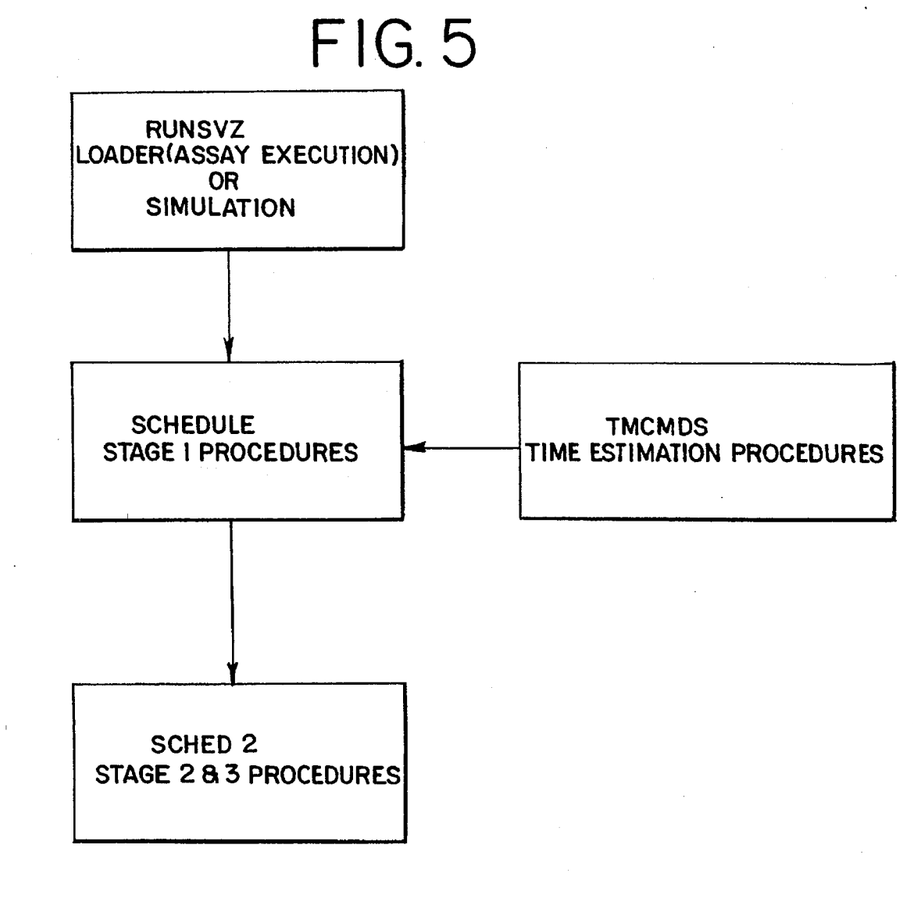
FIG. 5 is a block diagram flow chart depicting a portion of the program routines included on the module for operation of the embodiment of FIG. 1.

FIG. 5 is a flow chart illustrating the program routines for operating the analyzer and calling the scheduler routines. A first routine RUNSVZ begins the operation and performs certain initialization procedures. RUNSVZ calls the SCHEDULE program that includes the STAGE 1 procedures. Time estimations for performing "blocks" of commands are developed in the TMCMDS routine and output to the SCHEDULE file. SCHEDULE calls SCHED2 that includes STAGE 2 and STAGE 3 procedures. TMCMDS.LST, SCHEDULE.LST, and SCHED2.LST, are included in the Appendix of this specification.

Figure 6:
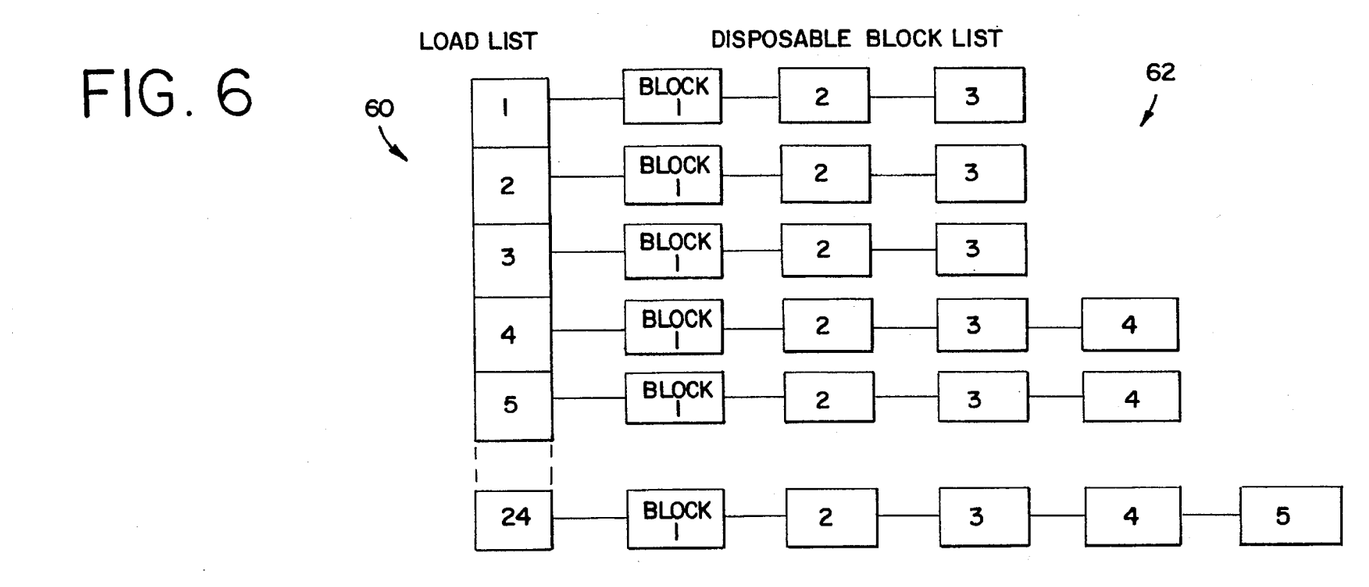
FIG. 6 is a diagram showing correspondence between a load list and lists of block descriptors associated with each specimen sample as developed by the STAGE 1 procedures of FIG. 4.

FIG. 6 is a diagram showing correspondence between the load list 60 and lists of block descriptors associated with each specimen sample as developed by the STAGE 1 procedures of FIG. 4. Based upon the entered load list, the STAGE 1 procedures develop time allowances for the operations to the performed by the analyzer unit instrument systems upon each specimen sample. The load list 60 indicates the sample specimen, e.g. Samples 1–24. The time allowances are organized into "time blocks", 1, 2, 3, associated with each of the samples. The time blocks represent one or more operations or activities to be performed by the analyzer systems upon or for that sample. Each specimen sample typically has associated with it several time blocks. For example, Sample 1 (as well as Samples 2 and 3) has three time blocks associated with it, Sample 4 has four time blocks associated with it, and Sample 24 has five time blocks associated with it. According to this embodiment of the invention, the time blocks establish when an analyzer unit resource (e.g. an instrument system) is occupied with a task associated with a sample. Accordingly, only one time block can take place (i.e. be performed) at a time.

Each of the time blocks of each specimen sample has "block descriptors" associated with it. The block descriptors contain information such as which sample the block is associated with, how much time will be allowed to perform the steps in this time block, and importantly, whether this block must be performed within a specific time limit or a specific range of time limits of other blocks associated with this sample.

In addition, the STAGE 1 time allowance procedures also assign a sequence number to each of the specimen samples. The sequence number arranges the samples by assay type. The sequence number is used to determine in what order the scheduler program, described below, undertakes the scheduling of the time blocks associated with each sample. The sequence number does not necessarily correspond to which assays are started first, but rather to which samples are scheduled first. When a combination of assays is made available for running together in one run in the biological analyzer, it can sometimes be determined which of the assays should be started first in order to provide the overall best through put. It has been found that, in general, consistently greater through put is achieved by scheduling assays of certain types first. This is usually a function of the types or number of steps (or time blocks) required to perform the assay as well as the incubation periods required between time blocks of the assay. Accordingly, the scheduler portion of the program begins the scheduling of the assays based on a predetermined priority among the assays. For example, when Prolactin, LH, and FSH assays are being performed on specimen samples loaded in a carousel rack, the scheduler first schedules the specimen samples upon which the Prolactin assay will be run regardless of the number of specimens designated for the Prolactin assay. The Prolactin assay is given priority because its time blocks and incubation periods afford relatively less flexibility for scheduling and experimentation has demonstrated that scheduling the Prolactin assay first increases overall throughput. Scheduler program schedules the time blocks of each of the specimen samples designated for the Prolactin assay before scheduling any of the time blocks of any of the specimen samples designated for other assays. If the steps for performing different assays were fairly similar in terms of number of steps and incubation periods, it would not necessarily be advantageous to begin assays of one type before assays of another type.

The time blocks associated with a specific sample are separated from each other by "intervals". In some cases, these "intervals" are fixed, i.e. the subsequent time block must begin at exactly a fixed period of time after the end of the previous time block for that sample. This may be due to constraints imposed by the chemical reactions involved in performing the assays. Such time blocks may be referred to as "linked". In other cases, the "intervals" between time blocks are flexible. With a flexible interval, a range of time is specified, i.e. the amount of time allowed between the end of a time block and the beginning of the subsequent time block can fall in a range between a minimum and a maximum time interval. The difference between the minimum and the maximum time interval is referred to as a "window". By utilizing the flexibility afforded by this "window" of time, the scheduler program can schedule operation of all the steps involved in performing the assays on the samples without exceeding any of the time limits as well as achieve an acceptable through put for operation of the analyzer.

In order to schedule the analyzer unit activities, the scheduler program does not necessarily attempt to schedule each time block at the earliest available time, i.e. at the minimum interval of the window. Instead, the scheduler program attempts to schedule each time block separated by windows so that the interval between the time blocks is calculated as a dynamic function of a number of load list parameters, including the number of tests being performed and the duration of selected blocks, among other considerations.

Figure 7:
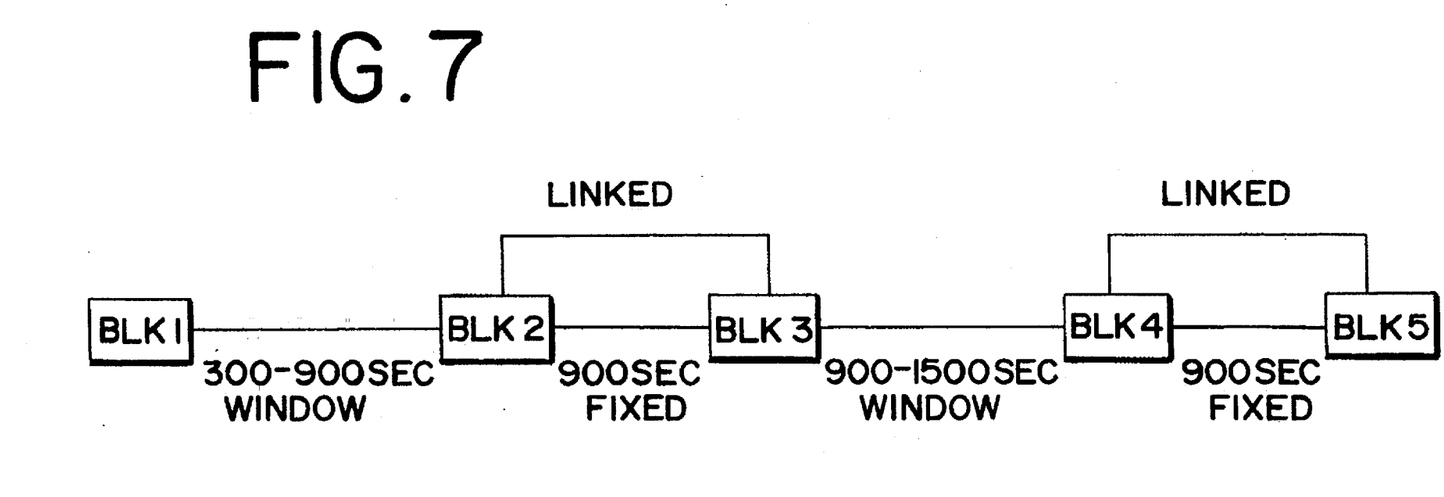
FIG. 7 is diagram depicting an example of the schedule blocks and interval periods for a single specimen sample to be scheduled in accordance with the STAGE 2 procedures of FIG. 4.

FIG. 7 a diagram of an example of time blocks, BLK 1, BLK 2, BLK 3, BLK 4 and BLK 5 associated with a single specimen sample. Adjacent time blocks are separated by intervals that are either fixed (i.e. the minimum interval time is equal to the maximum interval time, for example, between BLK 2 and BLK 3 or BLK 4 and BLK 5) or flexible (i.e. in which the minimum interval time is not equal to the maximum interval time, for example, between BLK 1 and BLK 2 or between BLK 3 and BLK 4). Time blocks separated by fixed interval times are considered "linked".

After the STAGE 1 procedures are completed, the scheduler program calls the STAGE 2 scheduler procedures. The STAGE 2 procedures actually develop the schedule for the time blocks generated by STAGE 1. The sample having the highest assigned priority sequence number is scheduled first. As mentioned above, the sequence number does not necessarily correspond to which assays are started first, but rather to which samples are scheduled first. It is evident however that the assay for the sample with the highest priority will begin first because it will be scheduled first and there will be no constraints on scheduling the time blocks of that sample. It is also likely that other assays for samples with high priorities will also tend to be begun sooner.

The scheduler calculates the interval between time blocks according to the following formula. This formula provides for a favorable through put. All variables apply to the sample being scheduled at that moment. $I_{min}$ (the Minimum Incubation Time applied to next block)

$$I_{min}=[(A-B)+1]*(C+D+E) +[(B-1)*(F+G+H)]$$

where,

A=the total number of samples being scheduled in the run, i.e. the total number of wedges on the carousel for that particular run.

B=the sequence number of the sample being processed at that particular time according to the scheduled sequence order.

C=the time allowance for the current time block or the longest time allowance for the time block of any previous time blocks of that sample being scheduled that are linked with a fixed incubation time, e.g. the current block time: pipetting time for the block currently being scheduled for that sample only; the previous block can be any block for that sample that occurs before the current block.

D=a "prep" (preparation) time that corresponds to the time that it takes, for example, to home the boom, move to the wash cup, move processing position to pipetting station, home syringes and valves before the beginning of each block, etc.; (This time is included in the calculation of the window since it is a mechanical activity that is executed prior to assay blocks. The current prep time used for all blocks is 2 seconds.

E=the rinse time associated with block chosen in for "C" above (or if the rinse time is optionally variable, the longest rinse time).

F=the next block length or longest block time of subsequent blocks linked with fixed incubation timer (i.e., the next block is the block following the current block of that sample). A subsequent block can be any block for that sample that occurs after the next block that is linked with fixed incubation time.

G=a prep time, as in "D" above this prep time associated with the block chosen in "F"; and H=the rinse time associated with block chosen in "F" (or if the rinse time is optionally variable, the longest rinse time).

According to the formula, the scheduler program compares the current (or next) block to the longest previous (or subsequent) block that is linked to another block with a fixed incubation time (i.e., no "window"). The longest of either is used in the formula. If previous (or subsequent) blocks do not exist; the scheduler program will use current (or next) blocks for the window calculation.

If the calculated minimum window is less than the actual minimum window, the actual minimum window is used.

In calculating the rinse time, as in "E" and "H", above, if the block that is used for the window calculation has an optional rinse operation, the rinse operation with the longest associated rinse time will be used.

Figure 8:
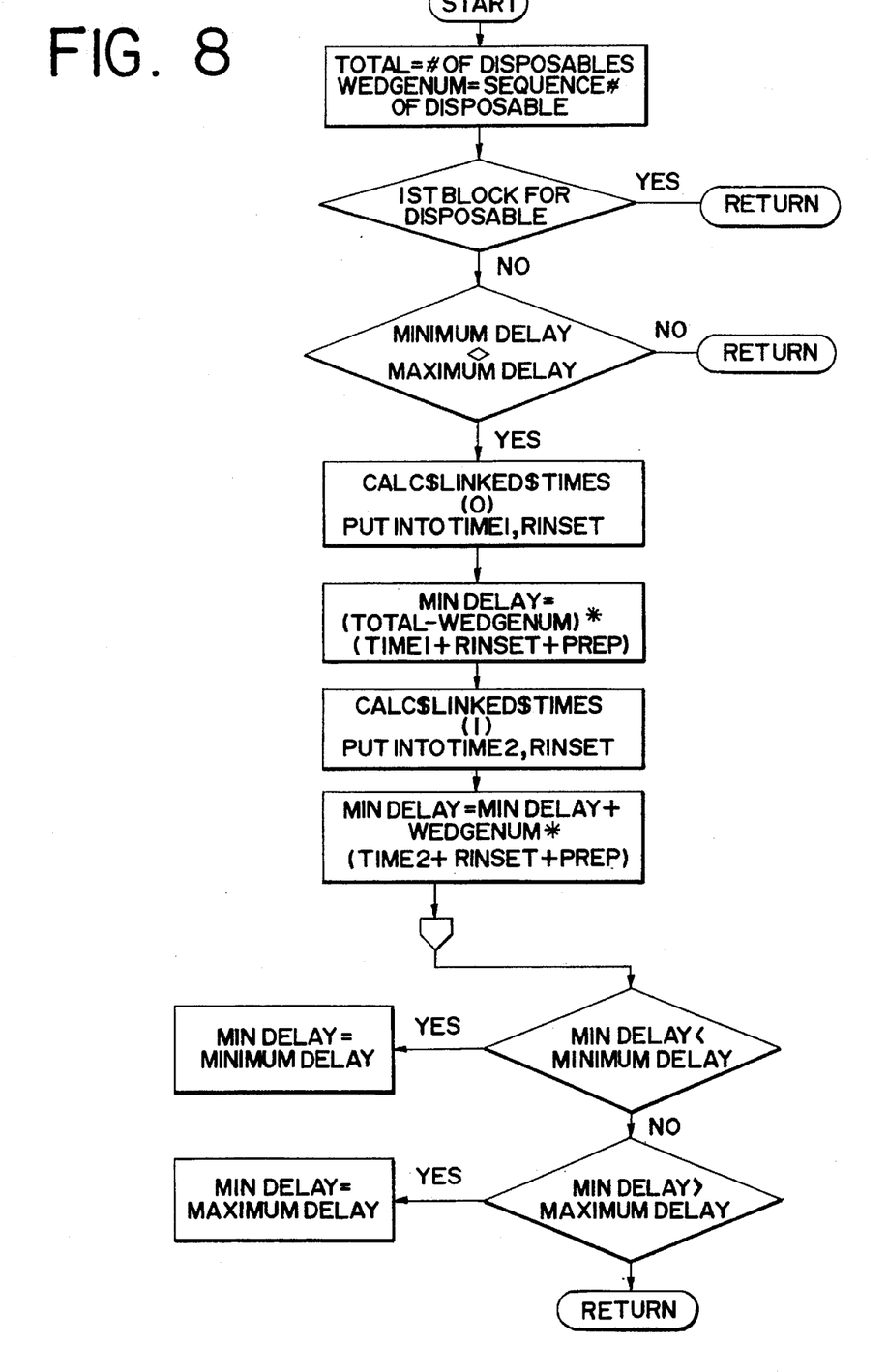
FIG. 8 is a flow chart of the portion of the program performed by the STAGE 2 procedures of FIG. 4 for determining the minimum interval period between two time blocks.

Referring to FIG. 8, there is a flow chart illustrating the operation of the portion of the scheduler program used to determine the minimum time interval following the formula set forth above. This portion of the program is included in the STAGE 2 procedures described above. The flow chart shown in FIG. 8 requires that the block descriptors for each pipetting block, the time estimations for each block, and the sorting the load list, i.e. the STAGE 1 procedures, have already been determined.

This part of the scheduler program establishes the minimum interval used for scheduling a time block for a specimen sample. The schedule developed for each specimen sample includes the time that each of the time blocks for that sample begins. This portion of the schedule loops, i.e. is run, for each time block of each specimen sample. The schedule for each specimen sample is determined one at a time until all the specimen samples are scheduled. Once the program fixes the schedule for a specimen sample and moves on to another specimen sample, the program does not go back and attempt to reschedule the time blocks of the prior specimen sample. A "first-fit" approach is used wherein once the schedule for a particular sample is "fitted", it is not rescheduled.

Referring again to FIG. 8, this portion of the scheduler program first determines how many (total="A" of formula) specimen samples (disposables) are in the carousel rack and the sequence number (wedgenum="B") of the specimen sample out of the total number is being scheduled. If the time block being scheduled is the first block for that specimen sample, it is tentatively assigned to the first available time slot with enough time to fit the block. This available time corresponds to a time when the instrument systems of the analyzer unit are not otherwise occupied with other specimen samples. This may correspond to a time period after completion of all the time blocks of previously scheduled specimen samples or to a time period corresponding to an incubation period between time blocks of previously scheduled samples. If this is the first time block, the program loops back to tentatively assign a start time for the next time block for that specimen sample.

For the second and subsequent time blocks for the specimen sample, the program proceeds to the next step. Unless a time block being scheduled must follow the previous time block by a fixed incubation period (i.e. is "linked"), the program calculates a preferred minimum incubation period. This is performed in the steps beginning with "CAL-C$LINKED$TIMES". This follows the formula set forth above. First, if there are any linked blocks for that specimen sample preceding the block being scheduled, "time1" corresponding to "C" and "rinset" corresponding to "E" are calculated. Then, if there are any linked blocks subsequent the block being scheduled, "time2" corresponding "F" and "rinset" corresponding to "G" are calculated. Then the minimum incubation time ("min delay") is calculated based upon the "total" minus the "wedgenum" times the "time1" plus the "rinset" plus the prep time. (Note that the "prep time", equal to "E" is a fixed time). If calculated "min delay" falls between the minimum and maximum delay allowed for that period, the calculated "min delay" is used. The incubation period is tentatively assigned and the next time block is tentatively assigned following the calculated incubation period. If the time block cannot be fitted with the calculated incubation period, the time block is scheduled for the next available time period in which it will fit. If this causes the incubation period to exceed the maximum allowable incubation period, the previously tentatively scheduled block for that specimen sample is reassigned to a later time period so that the maximum incubation time is not exceeded. Time blocks previous to the previous time block may have to be reassigned as well. The scheduler program proceeds in this manner until all the time blocks of all the samples are scheduled.

The portions of the program code corresponding to the flow chart of FIG. 8 for performing the determination of the minimum interval can be found in the Appendix in SCHED2.LST starting at line 946.

Referring again to FIG. 4, after the STAGE 2 procedures are completed, including the determination of the minimum intervals between time blocks and the scheduling of the time blocks, STAGE 3 procedures are performed. STAGE 3 procedures include the scheduling of necessary and appropriate rinse operations between time blocks.

Figure 9:
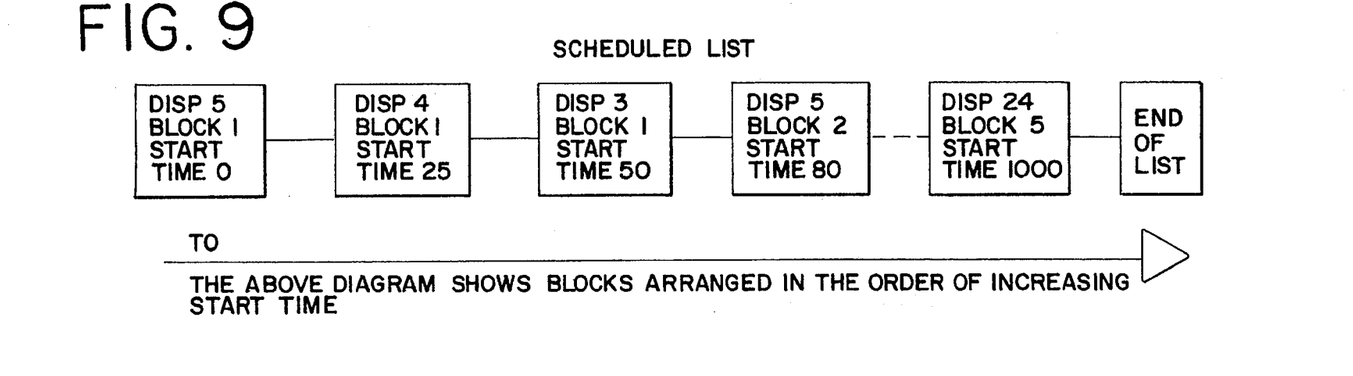
FIG. 9 is diagram depicting an example of a portion of the schedule blocks for all specimen samples to be scheduled and performed by the analyzer of FIG. 1.

FIG. 9 depicts a diagram illustrating an example of a portion of the sequence of time blocks scheduled by the scheduler program, above. Note that a start time has been assigned to each time block. The analyzer can then use the scheduled time blocks to perform the assays of the specimen samples.

After the schedule is complete the analyzer unit can run the assays following the developed schedule. At the end of the instrument system operations and output of the data, the assays are completed.

EXAMPLE 1

As explained above, for purposes of simplifying operation, the operator-user is instructed to group together the specimen samples for each of the different assay types. For example, if Prolactin, LH, and FSH assays are being run on specimen samples loaded in the carousel rack, the specimen samples upon which the Prolactin assay is to be run are grouped in adjacent positions in the carousel. This has the advantage of helping the user organize the samples and enter the load list.

A typical load is shown below:

Number samples on carousel: 24

LH: Positions 1–10

FSH: Positions 11–17

Prolactin: Positions 18–24

Prolactin is prioritized over LH and FSH.

Block #1 of position #5 (LH sample #5) is being scheduled. Since all the samples on which the Prolactin assay are scheduled first, position #5 is actually the 12th sample processed or scheduled.

| LH Block | Incubation Time | Block Length | Rinse Option | Time |
|---|---|---|---|---|
| 1 | 300–2100s | 18s | 0 | (5 s) |
| 2 | 300–2100s | 12s | 1 | (3 s) |
|   |           |     | 2 | (6 s) |
| 3 | 900s      | 15s | 1 | (3 s) |
|   |           |     | 2 | (6 s) |
| 4 | —         | 24s | N/A | (0 s) |

The values used for the formula to determine the minimum time interval ("window") are provided below:

A=24 (number of wedges on the carousel)

B=12 (the sequence number)

C=18 sec (Since block #1 is the first block and there are no previous blocks, the block length of #1 is used).

D=3 sec (Preparation time)

E=5 sec (the rinse time for block #1)

F=24 sec (Since block #2 is followed by 2 blocks linked with a fixed incubation time, the lengths of blocks 2, 3 and 4 are compared and the longest is chosen, i.e., Block #4).

G=3 sec (preparation time)

H=0 sec (Since no rinse option is in block #4, the rinse time is 0 sec).

Using the equation discussed above, the Minimum incubation time for block #1 is set equal to $$[(24-12)+1]*(18s+3s+5s) +[(12-1)*(24s+3s+0s)]=635 \text{ sec}$$

In a further embodiment of the present invention, a "paneling" feature could be provided. With "paneling", separate patient samples would not have to be prepared when it is desired to run several different assays on the same patient's sample. To provide this feature, one or more disposable cartridges not containing any patient specimen sample could be loaded into the carousel rack in addition to the cartridge containers having patient specimen sample. The fluid moving system of the analyzer would then move portions of the patient's specimen sample from the one disposable in which it had been provided, and pipette it to the disposables not containing the patient's sample. Thus, the analyzer unit can relieve the operator or others from the need for preparing separate containers.

As can be appreciated, with the embodiment of the present invention described above, the through put of an analyzer can be improved by minimizing idle time. With the embodiment described above, a favorable though put is achieved as well as reliable and consistent performance.

Although the present invention has been described in terms of a biological analyzer that operates automatically and unattended (e.g. in a "walk-away" mode in which the technician does not add or remove specimens during a run), it is understood that the present invention can readily be adapted to an "interruptable" mode analyzer in which the processing of the samples during a run can be interrupted so that an additional sample may be added. In such an analyzer, the processing program would modify the interrupted schedule so that the desired assay could be performed on the added specimen sample in a similar manner as if it were part of the original load list.

Although the embodiments of the present invention described above have particular advantage in a biological analyzer that runs more than one assay in a run, the present invention may be used as well in a biological analyzer operating with only one type of assay. With only one type of assay, the present invention may provide improved throughput, especially for example, when the biological analyzer is operated with less than a full carousel.

It is intended that the foregoing detailed description be regarded as illustrated rather than limiting and that it is understood that the following claims including all equivalents are intended to define the scope of the invention.

We claim:

1. In an analyzer having an analyzer unit into which a plurality of biological samples can be loaded for performing an assay of each of the samples, analyzer instrument systems in the unit for handling the samples and one or more reagents for conducting the assays, and means for operating the instrument systems to automatically perform operations to conduct the assay of each of the samples loaded into the analyzer, the improvement comprising:

means for developing a schedule for performing the operations to be executed by the analyzer instrument systems, said schedule developing means comprising:
   means for automatically and adaptively calculating an interval period between at least two operations performed by the analyzer instrument systems on at least one of the biological samples as a function of an entered load list unless a fixed interval period between operations is required; and
   means for scheduling instrument system operations and the calculated interval periods.

2. The improved analyzer of claim 1 in which the means for calculating interval periods further comprises:

means for automatically and adaptively calculating interval periods between at least two operations performed by the analyzer instrument systems on at least one of the biological samples as a function of a total number of specimen samples in the analyzer.

3. The improved analyzer of claim 1 further comprising:

means for determining a sequence list of biological samples from the entered load list specifying a sequence list position related to at least one of the biological samples;

and in which the means for scheduling instrument system operations further comprises:

means for scheduling the operations performed by the analyzer instrument systems for each biological sample based upon the sequence list position of said sample.

4. The improved analyzer of claim 3 in which the means for calculating interval periods further comprises:

means for automatically and adaptively calculating interval periods between two operations performed by the analyzer instrument systems on at least one of the biological samples as a function of the sequence list position of the sample being scheduled.

5. The improved analyzer of claim 1 further comprising:

means for developing a list of time blocks having block descriptors for at least one sample from the entered load list, said time block descriptors including a time allowance for performing operations related to a sample;

and in which the means for calculating interval periods further comprises the step of:

means for calculating an interval period between a current time block and a subsequent time block for said sample.

6. The improved analyzer of claim 5 in which the means for calculating an interval period further comprises:

means for automatically and adaptively calculating interval periods between two operations performed by the analyzer instrument systems on a biological sample as a function of the time allowance for a current time block unless a previous time block for said sample is linked to another time block by a fixed interval period in which case said interval period is a function of the time block having a greatest time allowance of the linked time blocks and the current time block.

7. The improved analyzer of claim 5 in which the means for calculating an interval period further comprises:

means for automatically and adaptively calculating interval periods between two operations performed by the analyzer instrument systems on a biological sample as a function of a time allowance for a rinse time associated with the current time block unless a previous time block for said sample is linked to another time block by a fixed interval period in which case said interval period is a function of a rinse time associated with the time block having a greatest time allowance of the linked time blocks and the current time block.

8. The improved analyzer of claim 5 in which the means for calculating an interval period further comprises:

means for automatically and adaptively calculating interval periods between two operations performed by the analyzer instrument systems on a biological sample as a function of a time allowance for the current time block unless a subsequent time block for said sample is linked to another time block by a fixed interval period in which case said interval period is a function of the time block having a greatest time allowance of the linked time blocks and the current time block.

9. The improved analyzer of claim 5 in which the means for calculating an interval period further comprises the step of:

means for automatically and adaptively calculating interval periods between two operations performed by the analyzer instrument systems on a biological sample as a function of a time allowance for a rinse time associated with the current time block unless a subsequent time block for said sample is linked to another time block by a fixed interval period in which case said interval period is a function of a rinse time associated with the time block having a greatest time allowance of the linked time blocks and the current time block.

10. The improved analyzer of claim 5 in which the means for scheduling instrument system operations further comprises:

means for scheduling the time blocks for performing operations to perform an assay on a first sample, said first sample having priority based upon said first sample's sequence on said load list;

means for scheduling the time blocks for performing analyzer system operation to perform each additional assay on each additional sample before, between, or after the scheduled time blocks of previously scheduled samples, said means for scheduling of time blocks for each additional sample based upon the priority of each sample on said load list.

11. The improved analyzer of claim 5 in which the means for scheduling instrument system operations further comprises:

means for tentatively scheduling the time blocks for a single sample until all the time blocks for said single sample are tentatively scheduled; and means for fixing the scheduled time blocks for that sample.

12. The improved analyzer of claim 11 in which the means for tentatively scheduling further comprises:

means for recursively rescheduling a previously tentatively scheduled time block of that sample in order to tentatively schedule a time block.

13. The improved analyzer of claim 1 in which the means for calculating interval periods further comprises:

means for calculating an interval period between two operations performed by the analyzer instrument systems on at least one of the biological samples wherein the interval period is calculated to be no less than:

$$[(A-B)+1] \times (C+D+E) + [(B-1) \times (F+G+H)]$$

where

A=a total number of samples being scheduled in a run;

B=a sequence number of the sample being processed at that particular time according to a scheduled sequence order;

C=a time allowance for a current time block or longest time allowance for a time block of previous time blocks linked with a fixed incubation timer;

D=a preparation time;

E=a longest rinse time associated with block chosen in C above;

F=a next block length or longest block time of subsequent blocks linked with fixed incubation timers;

G=a preparation time; and

H=a longest rinse time associated with block chosen in F.

14. The improved analyzer of claim 1 wherein the entered load list indicates more than one type of assay to be performed on the biological samples.

15. The improved analyzer of claim 1 wherein the assays of the biological samples are performed in an unattended run.

16. In a method for operating a biological sample analyzer having analyzer instrument systems to perform assays of samples loaded therein, the improvement comprising the steps of:

automatically and adaptively calculating an adjustable interval period between two operations performed by the analyzer instrument systems on at least one of the biological samples as a function of an entered load list unless a fixed interval period between operations is required; and scheduling instrument system operations and the calculated interval periods.

17. The improved method of claim 16 in which the step of calculating interval periods further comprises the step of:

automatically and adaptively calculating interval periods between two operations performed by the analyzer instrument systems on at least one of the biological samples as a function of a total number of specimen samples in the analyzer.

18. The improved method of claim 16 further comprising the step of:

determining a sequence list of biological samples from the entered load list specifying a sequence list position related to at least one of the biological samples; and in which the step of scheduling instrument system operations further comprises:

scheduling the operations performed by the analyzer instrument systems for biological sample based upon the sequence list position related thereto.

19. The improved method of claim 18 in which the step of calculating interval periods further comprises the step of:

automatically and adaptively calculating interval periods between two operations performed by the analyzer instrument systems on at least one of the biological samples as a function of the sequence list position of the sample being scheduled.

20. The improved method of claim 16 further comprising the step of:

developing a list of time blocks having block descriptors for at least one sample from the entered load list, said time block descriptors including a time allowance for performing operations related to a sample;

and in which the step of calculating interval periods further comprises the step of:

calculating an interval period between a current time block and a subsequent time block for said sample.

21. The improved method of claim 20 in which the step of calculating an interval period further comprises the step of:

automatically and adaptively calculating interval periods between two operations performed by the analyzer instrument systems on a biological sample as a function of the time allowance for a current time block unless a previous time block for said sample is linked to another time block by a fixed interval period in which case said interval period is a function of the time block having a greatest time allowance of the linked time blocks and the current time block.

22. The improved method of claim 20 in which the step of calculating an interval period further comprises the step of:

automatically and adaptively calculating interval periods between two operations performed by the analyzer instrument systems on a biological sample as a function of a time allowance for a rinse time associated with the current time block unless a previous time-block for said sample is linked to another time block by a fixed interval period in which case said interval period is a function of a rinse time associated with the time block having a greatest time allowance of the linked time blocks and the current time block.

23. The improved method of claim 20 in which the step of calculating an interval period further comprises the step of:

automatically and adaptively calculating interval periods between two operations performed by the analyzer instrument systems on a biological sample as a function of a time allowance for the current time block unless a subsequent time block for said sample is linked to another time block by a fixed interval period in which case said interval period is a function of the time block having a greatest time allowance of the linked time blocks and the current time block.

24. The improved method of claim 20 in which the step of calculating an interval period further comprises the step of:

automatically and adaptively calculating interval periods between two operations performed by the analyzer instrument systems on a biological sample as a function of a time allowance for a rinse time associated with the current time block unless a subsequent time block for said sample is linked to another time block by a fixed interval period in which case said interval period is a function of a rinse time associated with the time block having a greatest time allowance of the linked time blocks and the current time block.

25. The improved method of claim 20 in which the step of scheduling instrument system operations further comprises:

scheduling the time blocks for performing operations to perform an assay on a first sample, said first sample having priority based upon said first sample's sequence on said load list;

scheduling the time blocks for performing analyzer system operation to perform each additional assay on each additional sample before, between, or after the scheduled time blocks of previously scheduled samples, said scheduling of time blocks for each additional sample based upon the priority of each sample on said load list.

26. The improved method of claim 20 in which the step of scheduling instrument system operations further comprises:

tentatively scheduling the time blocks for a single sample until all the time blocks for said single sample are tentatively scheduled; and fixing the scheduled time blocks for that sample.

27. The improved method of claim 26 in which the step of tentatively scheduling further comprises:

recursively rescheduling previously tentatively scheduled time blocks of that sample in order to tentatively schedule a time block.

28. The improved method of claim 16 in which the step of calculating interval periods further comprises the step of:

calculating an interval period between two operations performed by the analyzer instrument systems on at least one of the biological samples wherein the interval period is calculated to be no less than:

$$[(A-B)+1] \times (C+D+E) + [(B-1) \times (F+G+H)]$$

where

A = a total number of samples being scheduled in a run;

B = a sequence number of the sample being processed at that particular time according to a scheduled sequence order;

C = a time allowance for a current time block or longest time allowance for a time block of previous time blocks linked with a fixed incubation timer;

D = a preparation time;

E = a longest rinse time associated with block chosen in C above;

F = a next block length or longest block time of subsequent blocks linked with fixed incubation timers;

G = a preparation time; and

H = a longest rinse time associated with block chosen in F.

29. The improved method of claim 16 wherein the entered load list indicates more than one type of assay to be performed on the biological samples.

30. The improved method of claim 16 wherein the assays of the biological samples are performed in an unattended run.

* * * * *

UNITED STATES PATENT AND TRADEMARK OFFICE
CERTIFICATE OF CORRECTION

PATENT NO. : 5,576,215
DATED : November, 19, 1996
INVENTOR(S) : Burns, et. Al.

It is certified that error appears in the above-indentified patent and that said Letters Patent is hereby corrected as shown below:

Column 15, line 7, before "interval" insert --adjustable--.

Signed and Sealed this

Eighteenth Day of March, 1997

Attest:

BRUCE LEHMAN

Attesting Officer

Commissioner of Patents and Trademarks